(12) United States Patent
LeBlanc

(10) Patent No.: US 9,134,273 B2
(45) Date of Patent: Sep. 15, 2015

(54) METHODS FOR SELECTIVE DETECTION OF BIOLOGICALLY RELEVANT ACIDS

(71) Applicant: DH Technologies Development Pte. Ltd., Singapore (SG)

(72) Inventor: Yves LeBlanc, Newmarket (CA)

(73) Assignee: DH Technologies Development Pte. Ltd., Singapore (SG)

( * ) Notice: Subject to any disclaimer, the term of this patent is extended or adjusted under 35 U.S.C. 154(b) by 0 days.

(21) Appl. No.: 14/397,236

(22) PCT Filed: May 17, 2013

(86) PCT No.: PCT/IB2013/000965
§ 371 (c)(1),
(2) Date: Oct. 27, 2014

(87) PCT Pub. No.: WO2013/171571
PCT Pub. Date: Nov. 21, 2013

(65) Prior Publication Data
US 2015/0108343 A1    Apr. 23, 2015

Related U.S. Application Data

(60) Provisional application No. 61/649,063, filed on May 18, 2012.

(51) Int. Cl.
*G01N 33/50* (2006.01)
*B01D 59/44* (2006.01)
*G01N 27/62* (2006.01)
*H01J 49/00* (2006.01)

(52) U.S. Cl.
CPC ............ *G01N 27/622* (2013.01); *G01N 27/624* (2013.01); *G01N 33/50* (2013.01); *H01J 49/00* (2013.01)

(58) Field of Classification Search
USPC ................ 250/281–283, 286–288, 292, 299; 436/127–130, 173; 422/44, 70, 89, 98; 93/234, 235, 256
See application file for complete search history.

(56) References Cited

U.S. PATENT DOCUMENTS

| | | | |
|---|---|---|---|
| 4,551,624 A | 11/1985 | Spangler et al. | |
| 5,032,721 A * | 7/1991 | Bacon et al. | 250/282 |
| 5,095,206 A * | 3/1992 | Bacon et al. | 250/282 |
| 5,234,838 A * | 8/1993 | Bacon, Jr. | 436/173 |
| 5,338,931 A * | 8/1994 | Spangler et al. | 250/287 |
| 6,774,360 B2 | 8/2004 | Guevremont et al. | |
| 2005/0085740 A1 | 4/2005 | Davis et al. | |
| 2009/0032701 A1 * | 2/2009 | Rodier | 250/282 |
| 2009/0078862 A1 | 3/2009 | Rodier et al. | |
| 2011/0068264 A1 | 3/2011 | Xu et al. | |
| 2011/0247494 A1 * | 10/2011 | Dinnage et al. | 95/92 |

OTHER PUBLICATIONS

International Search Report from International Patent Application No. PCT/IB2013/000965, dated Sep. 2, 2013.

\* cited by examiner

*Primary Examiner* — Bernard E Souw

(57) ABSTRACT

Methods and systems for performing ion mobility spectrometry are provided herein. In accordance with various aspects of the applicant's teachings, the methods and systems can provide for the separation of biologically relevant acids that may be difficult to separate with conventional MS techniques. In various aspects, methods and systems in accordance with applicant's teachings can enable a differential mobility spectrometer to resolve biologically relevant acids through the use of $CO_2$ as the drift gas in combination with Acetone.

20 Claims, 7 Drawing Sheets

CoV Mapping for Succinic acid and Methylmalonic acid with CO2 as curtain gas
(Acetone as modifier (1.5%) – DMR set to 10psi of N2 in both cases)

*Note 1 – size of bubble reflect ion intensity observed (based on absolute intensities recorded)*
*Observation – Base line (10% valey) separation is obtained at SV of 3600 between the 2 species*

METHODS FOR SELECTIVE DETECTION OF BIOLOGICALLY RELEVANT ACIDS

RELATED APPLICATION

This application claims priority to U.S. provisional application No. 61/649,063, filed on May 18, 2012, which is incorporated herein by reference in its entirety.

FIELD

The invention generally relates to mass spectrometry, and more particularly to methods and apparatus for the separation of acids using ion mobility spectrometry.

INTRODUCTION

Though mass spectrometry (MS) can be useful for quantifying the amount of a particular analyte in a sample, MS techniques are sometimes inadequate to discriminate between two ionic species. By way of example, methylmalonic acid (MMA), a dicarboxylic acid, has the chemical formula $C_4H_6O_4$ and is a clinical marker for cobalamin deficiency (i.e., Vitamin $B_{12}$ deficiency). Though clinical assays that quantify MMA in a patient's blood using gas chromatography-mass spectrometry (GC-MS) can be sensitive, they often lack specificity as a result of interference from endogenous levels of succinic acid (SA), also a dicarboxylic acid having the chemical formula $C_4H_6O_4$. Moreover, as shown below, SA exhibits identical major and minor fragment MRM transition as that of MMA and is also often present at much higher levels than MMA in biological samples such that it interferes with the detection/discrimination of MMA:

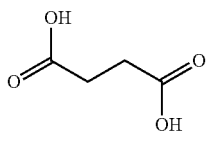

Succinic Acid (SA)
Molecular Formula = $C_4H_6O_4$
Monoisotopic Mass = 118.026609 Da
$[M-H]^- = 117.019332$ Da
Major Fragment = 73 Da
Minor Fragment = 55/99

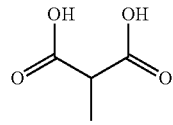

Methylmalonic Acid (MMA)
Molecular Formula = $C_4H_6O_4$
Monoisotopic Mass = 118.026609 Da
$[M-H]^- = 117.019332$ Da
Major Fragment = 73 Da
Minor Fragment = 55

Additional sample preparation methods such as derivatization prior to LC separation, solid-phase extraction, or turbulent-flow chromatography have been attempted to improve the separation of MMA from the more abundant SA. These techniques, however, require time consuming and/or complex sample preparation that can increase costs and/or decrease throughput, making clinical diagnostic quantification of MMA inaccurate, impractical, or unprofitable.

Because of the above-noted deficiencies of MS with respect to various analytes, techniques such as ion mobility spectrometry (IMS) are sometimes relied upon, in the alternative or in combination with MS, for improved sensitivity and selectivity. Whereas MS analyzes ions based on their mass-to-charge ratios, IMS instead separates ions based on the difference in the time required for ions to drift through a gas (typically at atmospheric pressure) in a constant electrostatic field applied along the axial length of a drift tube. In IMS, ions have a single motion of direction (axial) and are separated according to their mobility through the gas under these low field conditions (E<1000 V/cm). The drift time through the flight tube and therefore the mobility of an ion is characteristic of the size and shape of the ion and its interactions with the background gas.

Differential mobility spectrometry, also referred to as high field asymmetric waveform ion mobility spectrometry (FAIMS) or Field Ion Spectrometry (FIS), is a variant of IMS. In DMS, RF voltages, often referred to as separation voltages (SV), are applied across the drift tube in a direction perpendicular to that of the drift gas flow. Ions of a given species tend to migrate radially away from the axis of the transport chamber by a characteristic amount during each cycle of the RF waveform due to differences in mobility during the high field and low field portions. A DC potential, commonly referred to as compensation voltage (CV or CoV), applied to the drift tube provides a counterbalancing electrostatic force to that of the SV. The CV can be tuned so as to preferentially prevent the drift of a species of ion of interest. Depending on the application, the CV can be set to a fixed value to pass only ion species with a particular differential mobility while the remaining species of ions drift toward the electrodes and are neutralized. Alternatively, if the CV is scanned for a fixed SV as a sample is introduced continuously into the DMS, a mobility spectrum can be produced as the DMS transmits ions of different differential mobilities.

In IMS and DMS, molecules of the drift gas interact with the sample ions as they flow through the drift tube. Ideally, the drift gas is selected to interact with the various interfering analytes to further differentiate their mobilities. Additionally, modifier agents, which can be added to the drift gas, cluster with ions to different degrees during the high and low field portions of the SV, thereby shifting these ions' differential mobilities. However, the effects of DMS conditions on particular species are often unpredictable, with discrimination between overlapping detection peaks not always easily achieved. Indeed, DMS detection peaks of individual species are often quite broad relative to those of a mass spectrometer such that the overlap often interferes with species identification. By way of example, previous attempts to separate MMA and SA based on their mobility have been unsuccessful.

Accordingly, there remains a need for improved detection of biologically relevant acids with enhanced discrimination between species. Likewise, there remains a need for improved quantification of MMA from a sample while reducing sample preparation.

SUMMARY

It has been unexpectedly discovered that the use of $CO_2$ as the drift gas in a differential mobility spectrometer can advantageously allow resolving ion signals corresponding to isobaric carboxylic acids, including dicarboxylic acids such as MMA and SA. The resolution of the ion signals can in turn allow accurate quantification of such acids in a sample containing them. In many embodiments, such quantification of the isobaric dicarboxylic acids present in a sample can be achieved according to the teachings herein without the need for subjecting the sample to time-consuming preparations steps, such as derivatization. In some cases, the combination of $CO_2$ and a modifier such as acetone as the drift gas (e.g., in a concentration range of less than about 10%, from about 1% to about 10% of Acetone in gas volume, about 1.5% Acetone) unexpectedly and advantageously further enhances the resolution of ion signals corresponding to the isobaric carboxylic acids.

In accordance with one aspect, certain embodiments of the applicant's teachings relate to a method for performing ion mobility spectrometry. According to the method, a sample containing or suspected of containing an acidic analyte of interest can be transmitted into a differential mobility spectrometer. The sample can be transported through the differential mobility spectrometer using a drift gas comprising $CO_2$ and acetone to effect separation of ions of the acidic analyte of interest from ions of an interfering acidic analyte present in the sample.

In accordance with another aspect, certain embodiments of the applicant's teachings relate to a method for performing ion mobility spectrometry. According to the method, a sample containing or suspected of containing an acidic analyte of interest can be ionized to generate a plurality of analyte ions. The plurality of analyte ions can be transported using a drift gas comprising $CO_2$ through an ion mobility spectrometer to effect separation of ions of the acidic analyte of interest from ions of an interfering acidic analyte present in said ionized sample.

In some aspects, the drift gas can have a concentration of $CO_2$ greater than about 80%, greater than about 90%, greater than about 95%, or greater than 98.5%. In some aspects, the drift gas can consist essentially of $CO_2$. In various aspects, the drift gas can consist essentially of $CO_2$ and Acetone.

In various aspects, the ions of the acidic analyte of interest and the interfering acidic analyte can be isobaric. In some aspects the analyte of interest and the interfering analyte have a carboxylic acids function. In some aspects, the acidic analyte of interest and the interfering acidic analyte can comprise carboxylic acids. For example, the carboxylic acids can comprise leucine and isoleucine. In some aspects, the acidic analyte of interest can be MMA and the interfering acidic analyte can be SA.

In some aspects of various embodiments in accordance with the present teachings, the method can include supplying a modifier to the drift gas. The modifier can be a polar compound. For example, the modifier can comprise acetone.

In various aspects, the method can further include preparing a sample for ionization. For example, the sample can be either directly introduced by flow injection analysis (FIA) or dried onto a solid support for direct sample introduction such as, but not limited to AP-MALDI, DESI, DART and LDTD. In some aspects, the sample preparation does not include derivatization of the acidic analyte of interest. For example, the sample preparation comprises liquid chromatography.

In various aspects, the ion mobility spectrometer can comprise a differential mobility spectrometer, a FAIMS device, and/or can be coupled to a LC-MS/MS.

In accordance with another aspect, certain embodiments of the applicant's teachings relate to a method for performing ion mobility spectrometry. According to the method, a sample can be ionized to generate a plurality of analyte ions, the sample containing or suspected of containing an acidic analyte of interest. The plurality of analyte ions can be transported using a drift gas comprising $CO_2$ through an ion mobility spectrometer to resolve peaks of ions of said acidic analyte of interest from ions of an interfering acidic analyte present in said ionized sample.

In accordance with another aspect, certain embodiments of the applicant's teachings relate to a method for performing ion mobility spectrometry. According to the method, a sample containing MMA and SA can be ionized. A drift gas comprising $CO_2$ can be modified with acetone. The ionized sample can be transported using said modified drift gas through an ion mobility spectrometer to effect separation of the MMA from the SA, at least one of which can be quantified.

These and other features of the applicant's teachings are set forth herein.

BRIEF DESCRIPTION OF THE DRAWINGS

The skilled person in the art will understand that the drawings, described below, are for illustration purposes only. The drawings are not intended to limit the scope of the applicant's teachings in any way.

DETAILED DESCRIPTION

It will be appreciated that for clarity, the following discussion will explicate various aspects of embodiments of the applicant's teachings, while omitting certain specific details wherever convenient or appropriate to do so. For example, discussion of like or analogous features in alternative embodiments may be somewhat abbreviated. Well-known ideas or concepts may also for brevity not be discussed in any great detail. The skilled person will recognize that some embodiments of the applicant's teachings may not require certain of the specifically described details in every implementation, which are set forth herein only to provide a thorough understanding of the embodiments. Similarly it will be apparent that the described embodiments may be susceptible to alteration or variation according to common general knowledge without departing from the scope of the disclosure. The following detailed description of embodiments is not to be regarded as limiting the scope of the applicant's teachings in any manner.

Figure 1:
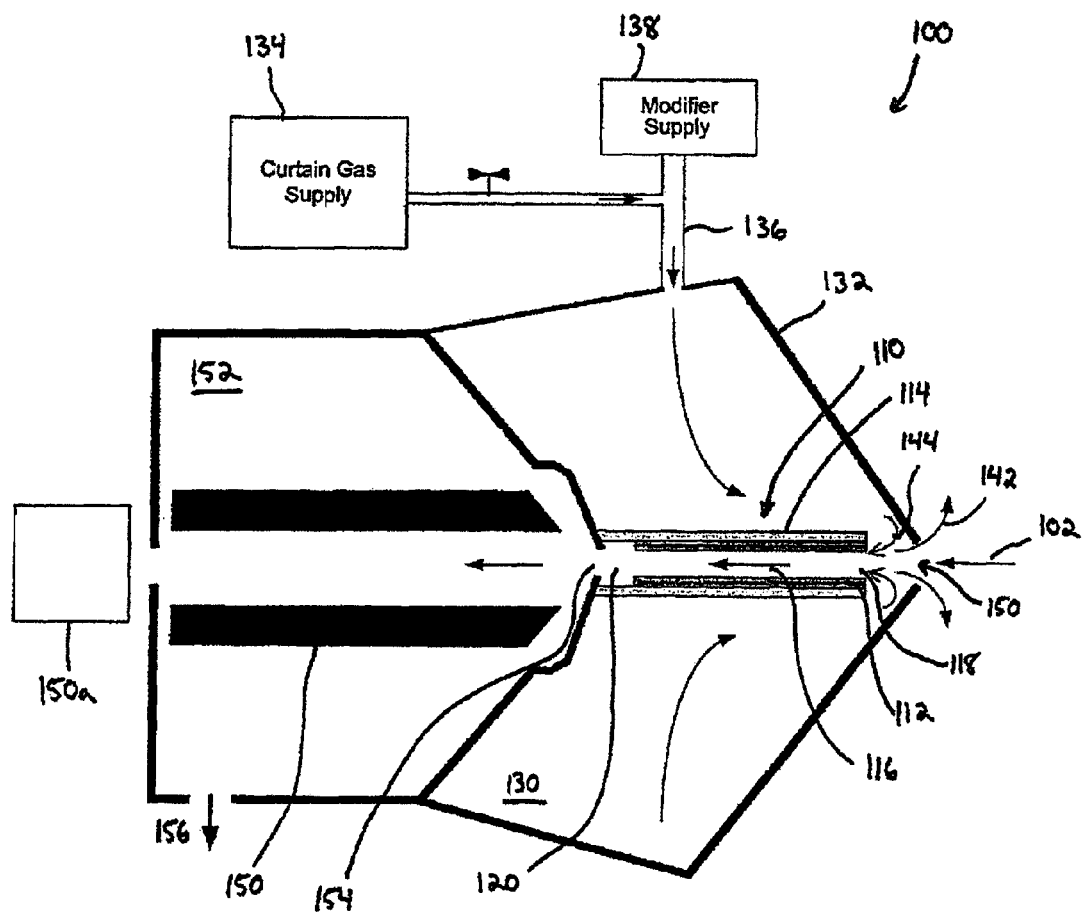
FIG. 1, in a schematic diagram, illustrates an exemplary differential mobility spectrometer/mass spectrometer system including a curtain gas supply and a modifier supply to the curtain gas in accordance with an aspect of various embodiments of the applicant's teachings.

Methods and systems for performing ion mobility spectrometry are provided herein. In accordance with various aspects of the applicant's teachings, the methods and systems can provide for the separation of biologically relevant acids, for example, that may be difficult to separate with conventional MS techniques. In various aspects, methods and systems in accordance with applicant's teachings can enable a differential mobility spectrometer to resolve a sample's biologically relevant acids such as isobaric dicarboxylic acids, leucine and isoleucine, and MMA and SA, all by way of non-limiting example With reference now to FIG. 1, an exemplary differential mobility spectrometer/mass spectrometer system 100 in accordance with various aspects of applicant's teachings is illustrated schematically. As shown in FIG. 1, the differential mobility spectrometer/mass spectrometer system 100 generally comprises a differential mobility spectrometer 110 in fluid communication with a first vacuum lens element 150 of a mass spectrometer (hereinafter generally designated mass spectrometer 150). As will be appreciated by a person skilled in the art, the differential mobility spectrometer/mass spectrometer system 100 represents only one possible configuration for use in accordance with various aspects of the systems, devices, and methods described herein. The mobility spectrometer 110 can have a variety of configurations, but is generally configured to resolve ions based on their mobility through a fixed or variable electric field. For example, the mobility spectrometer can be an ion mobility spectrometer, a differential mobility spectrometer, or FAIMS devices of various geometries such as parallel plate, curved electrode, or cylindrical FAIMS device, among others.

In the exemplary embodiment depicted in FIG. 1, the differential mobility spectrometer 110 comprises a pair of opposed electrode plates 112 surrounded by an electrical insulator 114 that supports the electrode plates 112 and insulates them from other conductive elements. The electrode plates 112 surround a drift gas 116 that drifts from an inlet 118 of the differential mobility spectrometer 110 to an outlet 120 of the differential mobility spectrometer 110. The outlet 120 of the differential mobility spectrometer 110 releases the drift gas 116 into an inlet 154 of a vacuum chamber 152 containing the mass spectrometer 150.

The differential mobility spectrometer 110 can be contained within a curtain chamber 130 that is defined by a curtain plate or boundary member 132 and is supplied with a curtain gas from a curtain gas supply 134. Specifically, curtain gas from curtain gas supply 134 can flow through curtain gas conduit 136 at flow rates determined by a flow controller and valves. The curtain gas supply 134 can provide any pure or mixed composition curtain gas to the curtain gas chamber. By way of non-limiting example, the curtain gas can be air, $O_2$, He, $N_2$, $CO_2$, or any combination thereof. In some aspects, the curtain gas can have a concentration of at least about 80% $CO_2$, at least about 90% $CO_2$, at least about 95% $CO_2$, at least about 98.5% $CO_2$, or substantially 100% $CO_2$.

The pressure of the curtain gases in the curtain chamber 130 can be maintained at or near atmospheric pressure (i.e., 760 Torr).

The system 100 can also include a modifier supply 138 for supplying a modifier to the curtain gas. As noted above, the modifier agents can be added to the curtain gas to cluster with ions differentially during the high and low field portions of the SV. As will be appreciated by a person skilled in the art, the modifier supply can be a reservoir of a solid, liquid, or gas through which the curtain gas is delivered to the curtain chamber 130. By way of example, the curtain gas can be bubbled through a liquid modifier supply. Alternatively, a modifier liquid or gas can be metered into the curtain gas, for example, through an LC pump, syringe pump, or other dispensing device for dispensing the modifier into the curtain gas at a known rate. For example, the modifier can be introduced using a pump so as to give a final concentration of about 1.5% for the modifier in the curtain gas. The modifier supply 134 can provide any modifier including, by way of non-limiting example, acetone, water, methanol, isopropanol, methylene chloride, methylene bromide, or any combination thereof.

Optionally, the curtain gas conduit 136 and/or curtain chamber 130 can include a heater for heating the mixture of the curtain gas and the modifier to further control the proportion of modifier in the curtain gas.

Ions 102 can be provided from an ion source (not shown) and emitted into the curtain chamber 130 via curtain chamber inlet 150. As will be appreciated by a person skilled in the art, the ion source can be virtually any ion source known in the art, including for example, a continuous ion source, a pulsed ion source, an atmospheric pressure chemical ionization (APCI) source, an electrospray ionization (ESI) source, an inductively coupled plasma (ICP) ion source, a matrix-assisted laser desorption/ionization (MALDI) ion source, a glow discharge ion source, an electron impact ion source, a chemical ionization source, or a photoionization ion source, among others. The pressure of the curtain gases in the curtain chamber 130 (e.g., ~760 Torr) can provide both a curtain gas outflow 142 out of curtain gas chamber inlet 144, as well as a curtain gas inflow 137 into the differential mobility spectrometer 110, which inflow 144 becomes the drift gas 116 that carries the ions 102 through the differential mobility spectrometer 110 and into the mass spectrometer 150 contained within the vacuum chamber 152, which can be maintained at a much lower pressure than the curtain chamber 130. For example, the vacuum chamber 152 can be maintained at a pressure of 2.3 Torr by a vacuum pump 156. As the curtain gas within the curtain chamber 130 can include a modifier, the drift gas 116 can also comprise a modifier. In an exemplary embodiment, the curtain gas/drift gas can be pure $CO_2$ modified with acetone.

As will be appreciated by a person skilled in the art, the mass spectrometer 150 can additionally include mass analyzer elements 150a downstream from vacuum chamber 152. Ions can be transported through vacuum chamber 152 and may be transported through one or more additional differentially pumped vacuum stages containing one or more mass analyzer elements 150a. For instance, in one embodiment, a triple quadrupole mass spectrometer may comprise three differentially pumped vacuum stages, including a first stage maintained at a pressure of approximately 2.3 Torr, a second stage maintained at a pressure of approximately 6 mTorr, and a third stage maintained at a pressure of approximately $10^{-5}$ Torr. The third vacuum stage can contain a detector, as well as two quadrupole mass analyzers with a collision cell located between them. It will be apparent to those skilled in the art that there may be a number of other ion optical elements in the system. Other type of mass analyzer such as single quadrupole, ion trap (3D or 2D), hybrid analyzer (quadrupole-time of flight, quadrupole-linear ion trap, quadrupole-orbitrap), orbitrap or time-of-flight, could also be used.

In operation, a sample (e.g., blood, serum, urine, saliva, etc.) containing or suspected of containing an acidic analyte of interest can be prepared in accordance with various methods as known in the art for introduction into the differential mobility spectrometer 110. The ions 102 can be generated adjacent the inlet 150 of the curtain chamber 130 and then transported through the differential mobility spectrometer 110 to effect separation of ions of the acidic analyte of interest from an interfering species. According to various aspects, the differential mobility spectrometer 110 can be operated at a fixed SV with the CV scanned so as to serially pass various ions. Alternatively, the applied CV can be selected to preferentially pass the acidic ion of interest based on, for example, a look up table based on known mobilities under the applied conditions. The ions transmitted by the differential mobility spectrometer can then be sent to downstream mass analyzer elements 150, 150a for further analysis or detection.

As will be appreciated by a person skilled in the art, a differential mobility spectrometer 110 can be utilized in various known systems modified in accord with the applicant's teachings. For example, with reference now to FIG. 2, there is illustrated in a schematic diagram, a differential mobility spectrometer system 200 in accordance with an aspect of a second embodiment of the present invention. For clarity, elements of the system 200 of FIG. 2 that are analogous to elements of the system 200 of FIG. 1 are designated using the same reference numerals as in FIG. 1, with 100 added. For brevity, the description of FIG. 1 is not repeated with respect to FIG. 2.

Figure 2:
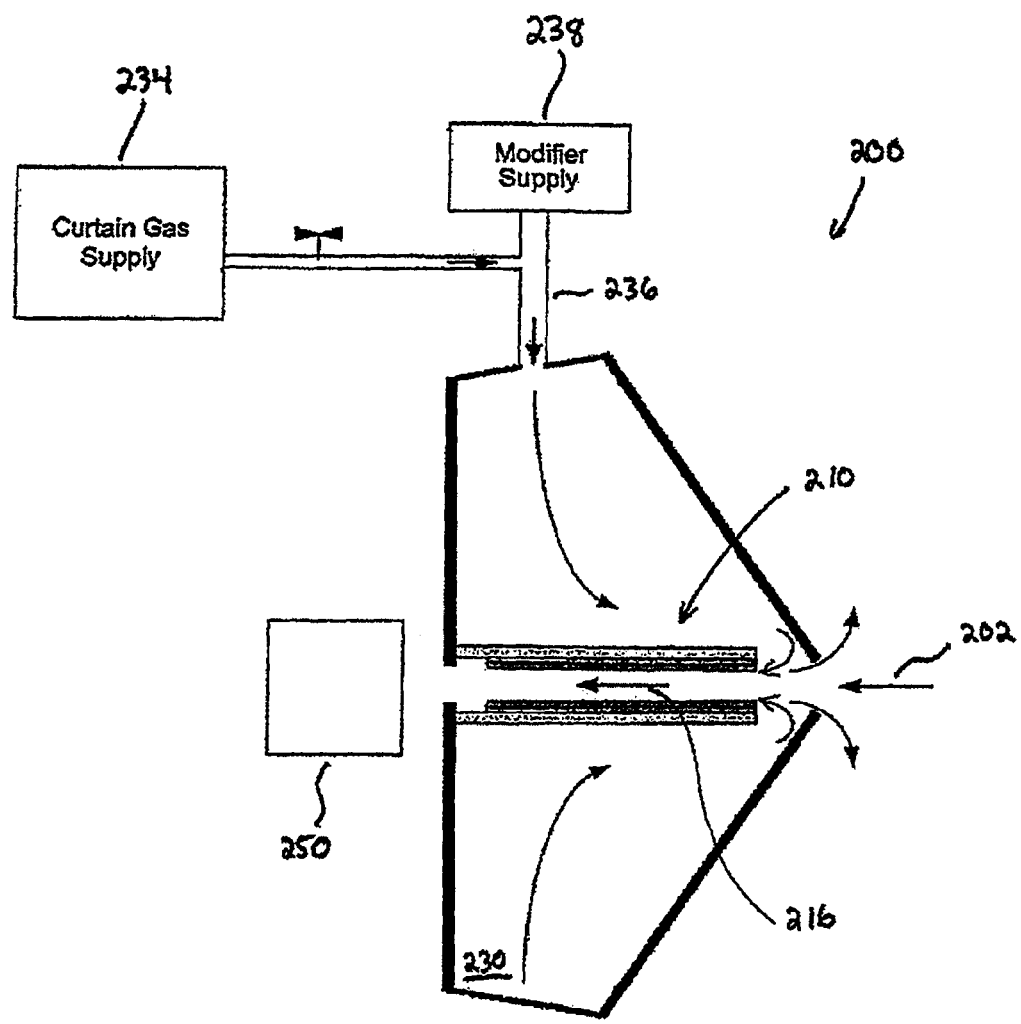
FIG. 2, in a schematic diagram, illustrates an exemplary differential mobility spectrometer system including a curtain gas supply and a modifier supply to the curtain gas in accordance with an aspect of various embodiments of the applicant's teachings.

As shown, the differential mobility spectrometer system 200 of FIG. 2 resembles a portion of the system 100 of FIG. 1, but lacks the downstream mass spectrometers 150, 150a and vacuum chamber element 152 of FIG. 1. Rather, the differential mobility spectrometer 210 can be installed upstream of any number of different mass spectrometer elements, or may simply be installed upstream of a region of reduced pressure that is effective to draw the ions 202 and drift gas 216 through the differential mobility spectrometer 210. Alternatively, a detector 250 (e.g., a Faraday cup or other ion current measuring device) disposed at the outlet 220 of the differential mobility spectrometer 210 can be effective to detect the ions transmitted by the differential mobility spectrometer 210.

The differential mobility spectrometer 210 is contained within a curtain chamber 230. The curtain chamber 230 can be supplied with a curtain gas from a curtain gas supply 234 modified by a modifier supply 138 in a manner similar to that described above in connection with FIG. 1.

EXAMPLES

The applicants' teachings can be even more fully understood with reference to the following examples and data presented in FIGS. 3-7, which demonstrate the separation of various biological acids present in a sample using differential mobility spectrometry in accordance with various aspects of the teachings herein. Other embodiments of the applicants' teachings will be apparent to those skilled in the art from consideration of the present specification and practice of the present teachings disclosed herein. It is intended that these examples be considered as exemplary only.

As noted above, MMA and SA are isobaric dicarboxylic acids present in biological samples such as blood. Though MMA is a known marker of Vitamin $B_{12}$ deficiency, mass spectrometric techniques often have difficulty with its specific quantification due to SA interference without costly and/or time-consuming sample preparation generally avoided in clinical diagnostic assays. With reference now to FIGS. 3-7, the data depict the results of using DMS to separate MMA from SA. Though the data depict the intensity of MMA and SA ions transmitted by the differential mobility spectrometer without downstream manipulation as discussed with reference to the system depicted in FIG. 2, a person skilled in the art will appreciate that an ion mobility spectrometer can alternatively be located on the front end of a mass spectrometer to enable further analysis of the transmitted ions.

Figure 3:
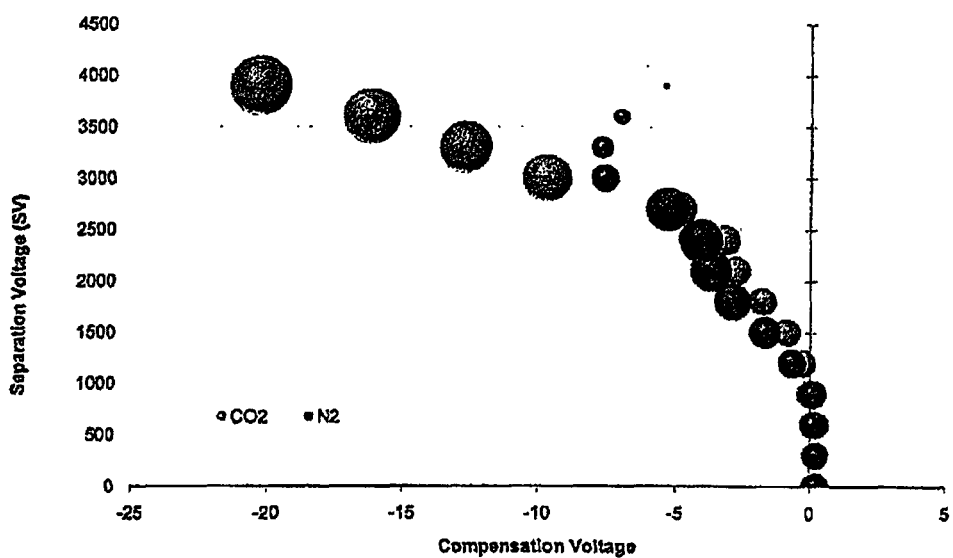
FIG. 3 depicts data comparing MMA ions transmitted by a differential mobility spectrometer with pure $N_2$ and pure $CO_2$ as the curtain gas and subsequently detected in accordance with aspects of various embodiments of the applicant's teachings.

With specific reference now to FIG. 3, this plot depicts the intensity of MMA ions (the size of each bubble reflects the absolute intensity of the detected ions) transmitted by a differential mobility spectrometer that is operated at various CV and SV as indicated by the x- and y-axis, respectively, with the use of pure $N_2$ and pure $CO_2$ as the curtain gas operated at gas flow of 3.3 L/min and $N_2$ throttle gas (DMR) operated at 0.3 L/min (10 psi) to increase the residence time in the differential mobility cell. No modifier was used. The differential mobility spectrometer was a SelexION™ modified to provide manual control via a calibrated flow controller for $CO_2$ gas. The ions were detected with a QTRAP® 5500 system marketed by AB Sciex.

As shown in FIG. 3, with pure $N_2$ as the curtain gas, MMA ions behave as b-type ions as indicated by their initial increase in mobility (i.e., the increasing amplitude of the CV) and followed by their subsequent decrease in mobility (i.e., the upper "tail") as the field strength increases. Moreover, the MMA ions exhibit significant intensity losses at high SV as indicated by the decreasing size of the bubbles. With pure $CO_2$ as the curtain gas, however, MMA ions exhibit both increased mobility and increased intensity at high SV.

Figure 4:
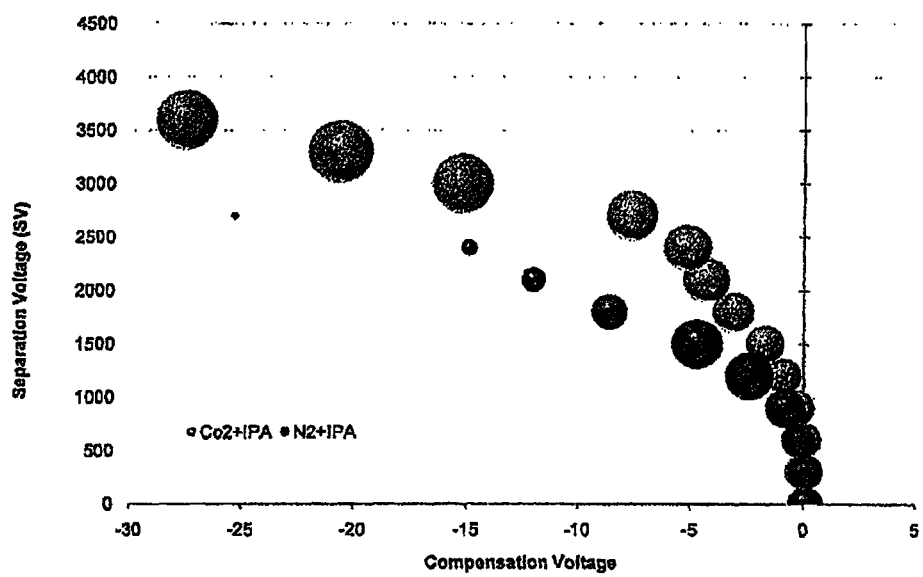
FIG. 4 depicts data comparing MMA ions transmitted by a differential mobility spectrometer with pure $N_2$ and pure $CO_2$ as the curtain gas and IPA as the modifier and subsequently detected in accordance with aspects of various embodiments of the applicant's teachings.

With reference now to FIG. 4, this plot depicts the intensity of MMA ions recorded at the outlet of a differential mobility spectrometer that is operated at similar conditions to that of FIG. 3 except with isopropyl alcohol (IPA, 1.5%) added to the curtain gas as a modifier. As shown in FIG. 4, with pure $N_2$+IPA as the curtain gas and modifier, MMA ions behave as a-type ions as indicated by their increasing mobility with increasing field strength. Nonetheless, the MMA ions still exhibit significant intensity losses at high SV. With pure $CO_2$+IPA as the curtain gas and modifier, however, MMA ions exhibit both increased mobility and increased intensity at high SV.

Figure 5:
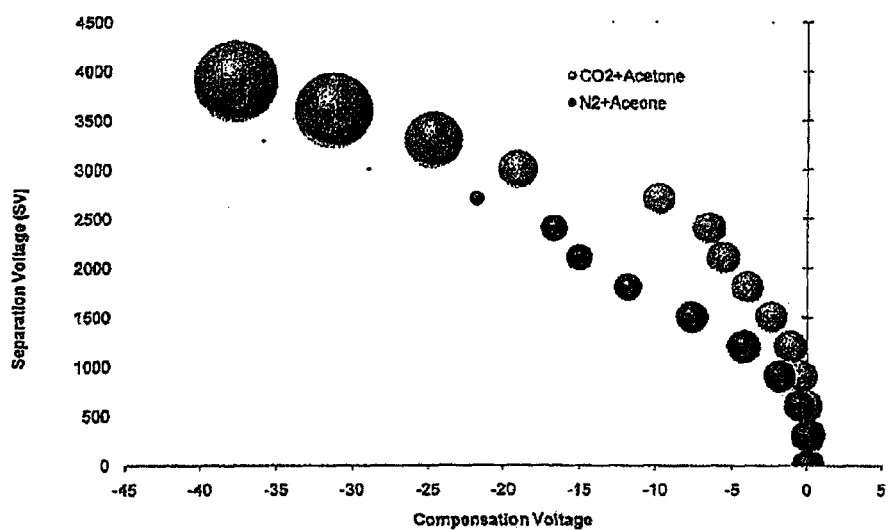
FIG. 5 depicts data comparing MMA ions transmitted by a differential mobility spectrometer with pure $N_2$ and pure $CO_2$ as the curtain gas and Acetone as the modifier and subsequently detected in accordance with aspects of various embodiments of the applicant's teachings.

With reference now to FIG. 5, this plot depicts the intensity of MMA ions recorded at the outlet of a differential mobility spectrometer that is operated at similar conditions to that of FIG. 4 except with acetone (1.5%) added to the curtain gas instead of IPA. As shown in FIG. 5, with pure $N_2$+Acetone as the curtain gas and modifier, MMA ions continue to behave as a-type ions as indicated by their increasing mobility with increasing field strength. However, the MMA ions exhibit even more significant intensity losses at high SV as compared to those shown by MMA ions with IPA as the modifier. With pure $CO_2$+Acetone as the curtain gas and modifier, the MMA ions exhibit both increased mobility and increased intensity at high SV.

Figure 6:
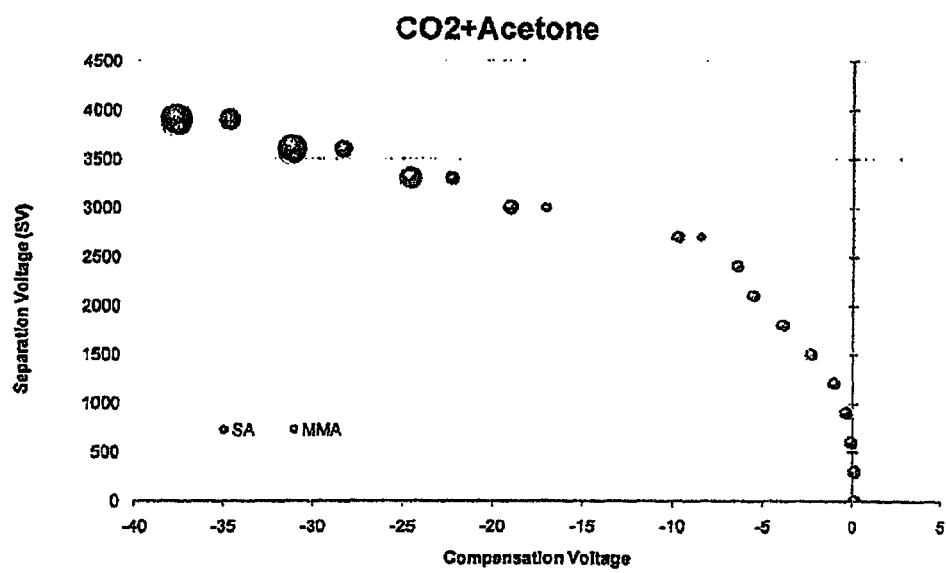
FIG. 6 depicts data comparing the transmission by a differential mobility spectrometer and subsequent detection of MMA ions and SA ions with pure $CO_2$ as the curtain gas and Acetone as the modifier in accordance with aspects of various embodiments of the applicant's teachings.

With reference now to FIG. 6, this plot depicts the intensity of both MMA and SA ions recorded at the outlet of a differential mobility spectrometer that is operated at similar conditions to that of FIG. 5. That is, each of MMA and SA ions were detected at the outlet end of the differential mass spectrometer with pure $CO_2$ as the curtain gas and Acetone (1.5%)

as the modifier. As shown in FIG. 6, both of the MMA ions and SA ions behaved as a-type ions as indicated by their increasing mobility with increasing field strength. However, at a given SV above about 2500V, the CVs for each of the species could be distinguished. For example, FIG. 6 indicates that at an SV of 3600V, there was about a 10% separation in the measured CV between MMA (−31.3V) and SA (−28.5V).

Figure 7:
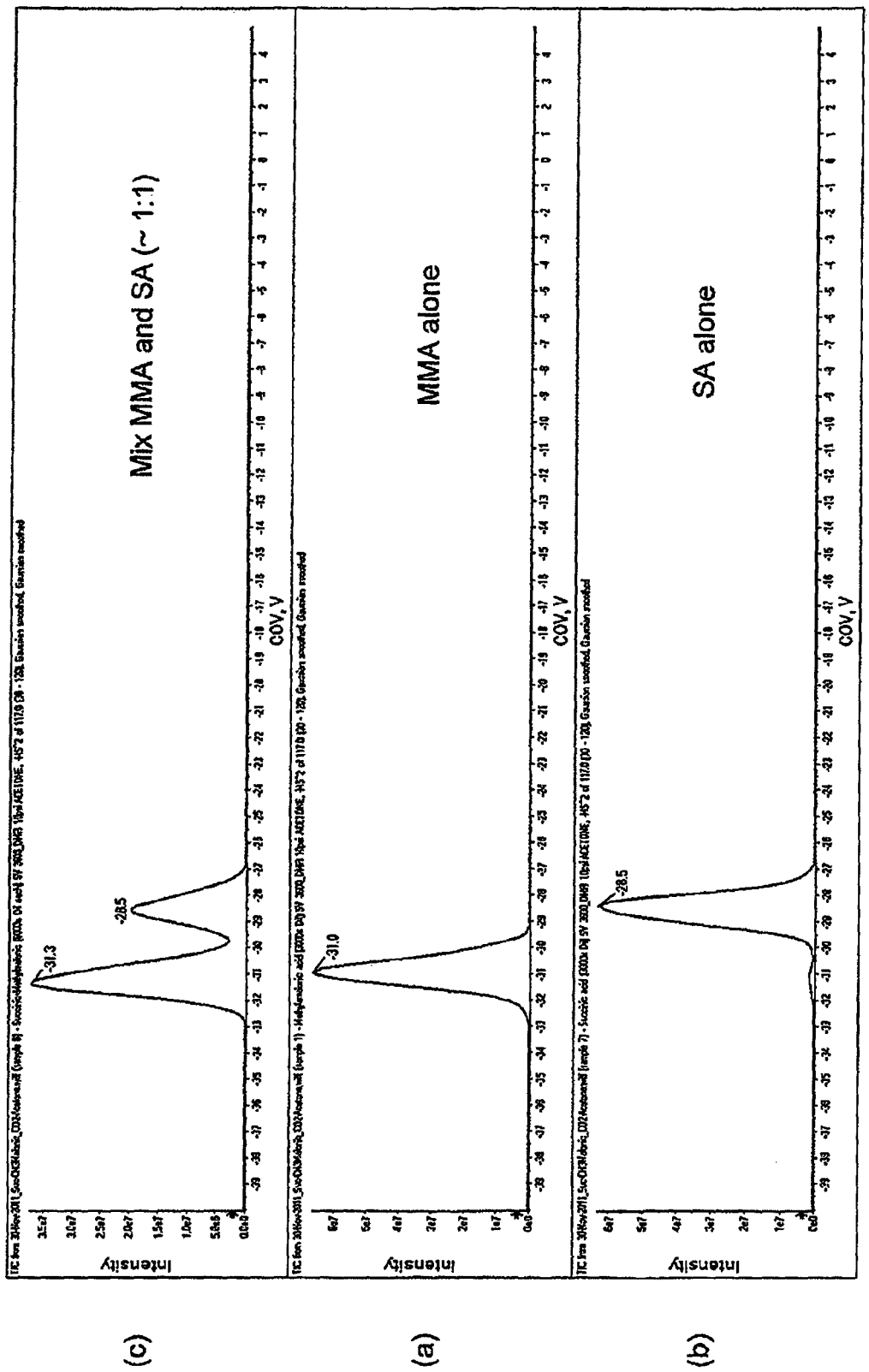
FIG. 7 depicts the mobility spectra of a differential mobility spectrometer of samples containing MMA and/or SA with pure $CO_2$ as the curtain gas and Acetone as the modifier in accordance with aspects of various embodiments of the applicant's teachings.

As shown in further detail in FIG. 7, a DMS operated with $CO_2$ as the curtain gas flowing through the DMS at a rate of 3 L/min with Acetone (1.5%) as the modifier can sufficiently separate MMA and SA from a single sample. With specific reference first to FIG. 7a, this plot depicts the count of detected ions transmitted from the DMS in a blank (water:methanol (50:50 (v:v)) with 0.1% formic acid) spiked with MMA only (~250 pg/μL) as the CV is scanned at a fixed SV of 3600V. A single peak appears in the mobility spectra at CV=−31.0V.

With reference now to FIG. 7b, this plot depicts the count of detected ions transmitted from the DMS in a blank (water:methanol (50:50 (v:v)) with 0.1% formic acid) spiked with SA only (~250 pg/μL) as the CV is scanned at a fixed SV of 3600V. A single peak appears in the mobility spectra at CV=−28.5V.

With reference now to FIG. 7c, this plot depicts the count of detected ions transmitted from the DMS in a blank (water:methanol (50:50 (v:v)) with 0.1% formic acid) spiked with MMA:SA (1:1) (each at ~250 pg/μL) as the CV is scanned at a fixed SV of 3600V. Two distinct peaks appear in the mobility spectra at CVs of −31.3V, which substantially corresponds to that of the peak detected in the sample containing only MMA as shown in FIG. 7a, and −28.5V, which substantially corresponds to that of the peak detected in the sample containing only SA as shown in FIG. 7b. The difference in the CV values for the transmission of MMA and SA is sufficient to permit selective monitoring/quantification of MMA without interference from SA.

Surprisingly, these data demonstrate that the combination of $CO_2$ as the drift gas and Acetone as the modifier agent increases the separation capability of the DMS for dicarboxylic acids. As a result, acids present in a single sample can be sufficiently resolved to allow for their specific quantification in accordance with the teachings herein, with minimal sample preparation.

The section headings used herein are for organizational purposes only and are not to be construed as limiting. While the applicant's teachings are described in conjunction with various embodiments, it is not intended that the applicant's teachings be limited to such embodiments. On the contrary, the applicant's teachings encompass various alternatives, modifications, and equivalents, as will be appreciated by those of skill in the art.

What is claimed is:

1. A method for performing ion mobility spectrometry, comprising:
   a. ionizing a sample to generate a plurality of analyte ions, the sample containing or suspected of containing an acidic analyte of interest; and
   b. transporting said plurality of analyte ions using a drift gas comprising $CO_2$ through an ion mobility spectrometer to effect separation of ions of said acidic analyte of interest from ions of an interfering acidic analyte present in said ionized sample.

2. The method of claim 1, wherein the drift gas has a concentration of $CO_2$ greater than about 80%.

3. The method of claim 1, wherein the drift gas has a concentration of $CO_2$ greater than about 98.5%.

4. The method of claim 1, wherein the drift gas consists essentially of $CO_2$.

5. The method of claim 1, wherein the acidic analyte of interest comprises methylmalonic acid (MMA).

6. The method of claim 5, wherein the interfering acidic analyte comprises succinic acid (SA).

7. The method of claim 1, wherein the ions of the acidic analyte of interest and the interfering acidic analyte are isobaric.

8. The method of claim 1, wherein the analyte of interest and the interfering analyte have a carboxylic acids function.

9. The method of claim 1, further comprising supplying a modifier to the drift gas.

10. The method of claim 9, wherein the modifier comprises a polar compound.

11. The method of claim 10, wherein the modifier comprises acetone.

12. The method of claim 1, further comprising preparing a sample for ionization.

13. The method of claim 12, wherein said sample preparation comprises drying said sample onto a solid support for direct sample introduction via any one of AP-MALDI, DESI, DART and LDTD.

14. The method of claim 1, wherein the ion mobility spectrometer comprises a differential mobility spectrometer.

15. The method of claim 1, wherein the ion mobility spectrometer comprises FAIMS.

16. The method of claim 1, wherein the ion mobility spectrometer is coupled to a LC-MS/MS.

17. The method of claim 1, wherein the ion mobility spectrometer is coupled to a LC-MS.

18. The method of claim 1, wherein step b comprises resolving peaks of ions of said acidic analyte of interest from ions of an interfering acidic analyte present in said ionized sample.

19. A method of mass spectrometry comprising:
   a. ionizing a sample containing MMA and SA;
   b. providing a drift gas comprising $CO_2$;
   c. modifying said drift gas with acetone;
   d. transporting said ionized sample using said modified drift gas through an ion mobility spectrometer to effect separation of MMA from SA; and
   e. quantifying at least one of MMA and SA.

20. A method for performing ion mobility spectrometry, comprising:
   a. introducing a sample containing or suspected of containing an acidic analyte of interest into a differential mobility spectrometer; and
   b. transporting said sample using a drift gas comprising $CO_2$ and acetone through said differential mobility spectrometer to effect separation of ions of said acidic analyte of interest from ions of an interfering acidic analyte present in said sample.

* * * * *